(12) United States Patent
Hapola et al.

(10) Patent No.: US 11,284,807 B2
(45) Date of Patent: Mar. 29, 2022

(54) ENGAGING EXERCISING DEVICES WITH A MOBILE DEVICE

(71) Applicant: Amer Sports Digital Services Oy, Vantaa (FI)

(72) Inventors: Tuomas Hapola, Vantaa (FI); Heikki Nieminen, Vantaa (FI); Mikko Martikka, Vantaa (FI); Erik Lindman, Vantaa (FI); Timo Eriksson, Vantaa (FI)

(73) Assignee: Amer Sports Digital Services Oy, Vantaa (FI)

( * ) Notice: Subject to any disclaimer, the term of this patent is extended or adjusted under 35 U.S.C. 154(b) by 0 days.

(21) Appl. No.: 16/427,401

(22) Filed: May 31, 2019

(65) Prior Publication Data

US 2019/0282103 A1    Sep. 19, 2019

Related U.S. Application Data

(63) Continuation-in-part of application No. 15/382,763, filed on Dec. 19, 2016, and a continuation-in-part of
(Continued)

(30) Foreign Application Priority Data

Dec. 21, 2015  (FI) ...................................... 20155989
Dec. 21, 2015  (GB) ...................................... 1522525
(Continued)

(51) Int. Cl.
*A61B 5/0245*    (2006.01)
*G16H 40/67*    (2018.01)
(Continued)

(52) U.S. Cl.
CPC .......... *A61B 5/0245* (2013.01); *A61B 5/0006* (2013.01); *A61B 5/0022* (2013.01);
(Continued)

(58) Field of Classification Search
CPC ... A61B 5/0245; A61B 5/0022; A61B 5/1118; A61B 5/681; A61B 5/0006;
(Continued)

(56) References Cited

U.S. PATENT DOCUMENTS 5,457,284 A    10/1995  Ferguson
5,503,145 A    4/1996   Clough
(Continued)

FOREIGN PATENT DOCUMENTS

AU    2007216704 A1    4/2008
CN        1877340 A1    12/2006
(Continued)

OTHER PUBLICATIONS

ARM big. Little. Wikipedia, The free encyclopedia, Oct. 11, 2018, Retrieved on May 28, 2020 from: <https://en.wikipedia.org/w/index.php?title=ARM_bit.LITTLE&oldid=863559211> foreword on p. 1, section "Run-state migration" on pp. 1-2.
(Continued)

*Primary Examiner* — Eyob Hagos
(74) *Attorney, Agent, or Firm* — Laine IP Oy (57) ABSTRACT

According to an example aspect of the present invention, there is provided an apparatus comprising at least one processing core, at least one memory including computer program code, the at least one memory and the computer program code being configured to, with the at least one processing core, cause the apparatus at least to receive a first sensor data stream from an exercising device, receive a second sensor data stream from a mobile device, correlate the first data stream with the second data stream, determine
(Continued)

that the exercising device is engaged with the mobile device, and provide indication to the exercising device and the mobile device that the devices are engaged with each other.

21 Claims, 7 Drawing Sheets

Related U.S. Application Data application No. 15/386,050, filed on Dec. 21, 2016, now Pat. No. 10,856,776, and a continuation-in-part of application No. 15/386,062, filed on Dec. 21, 2016, now Pat. No. 10,433,768, and a continuation-in-part of application No. 15/386,074, filed on Dec. 21, 2016, now Pat. No. 10,327,673.

(30) Foreign Application Priority Data

Sep. 20, 2016 (FI) .................................. 20165707
Sep. 20, 2016 (FI) .................................. 20165709
Sep. 20, 2016 (FI) .................................. 20165710

(51) Int. Cl.
| | |
|---|---|
| *A61B 5/00* | (2006.01) |
| *A61B 5/11* | (2006.01) |
| *G06K 9/00* | (2022.01) |
| *A61B 5/352* | (2021.01) |
| *G01C 22/00* | (2006.01) |
| *G01P 15/08* | (2006.01) |
| *A61B 5/024* | (2006.01) |

(52) U.S. Cl.
CPC ........ *A61B 5/02438* (2013.01); *A61B 5/1118* (2013.01); *A61B 5/352* (2021.01); *A61B 5/681* (2013.01); *G01C 22/006* (2013.01); *G01P 15/0802* (2013.01); *G06K 9/00342* (2013.01); *G16H 40/67* (2018.01); *A61B 5/7275* (2013.01); *A61B 2503/10* (2013.01)

(58) Field of Classification Search
CPC . A61B 5/02438; A61B 5/0456; A61B 5/7275; A61B 2503/10; A61B 5/1123; A61B 5/0205; A61B 5/024; A61B 5/02405; A61B 5/0024; G16H 40/67; G06K 9/00342; G01C 22/006; G01C 21/20; G01P 15/0802; A63B 69/0035; A63B 24/0062; A63B 2220/803; A63B 2230/06; A63B 2220/40; A63B 2024/0065; A63B 2024/0071; G06F 17/00
See application file for complete search history.

(56) References Cited

U.S. PATENT DOCUMENTS

| | | | |
|---|---|---|---|
| 5,924,980 A | 7/1999 | Coetzee | |
| 6,882,955 B1 | 4/2005 | Ohlenbusch et al. | |
| 7,627,423 B2 | 12/2009 | Brooks | |
| 7,706,973 B2 | 4/2010 | McBride et al. | |
| 7,721,118 B1 | 5/2010 | Tamasi et al. | |
| 7,917,198 B2 | 3/2011 | Ahola et al. | |
| 7,938,752 B1 | 5/2011 | Wang | |
| 8,052,580 B2 | 11/2011 | Saalasti et al. | |
| 8,323,188 B2 | 12/2012 | Tran | |
| 8,328,718 B2 | 12/2012 | Tran | |
| 8,538,693 B2 | 9/2013 | McBride et al. | |
| 8,612,142 B2 | 12/2013 | Zhang | |
| 8,655,591 B2 | 2/2014 | Van Hende | |
| 8,781,730 B2 | 7/2014 | Downey et al. | |
| 8,949,022 B1 * | 2/2015 | Fahrner | G01C 21/20 |
| | | | 701/433 |
| 9,008,967 B2 | 4/2015 | McBride et al. | |
| 9,107,586 B2 | 8/2015 | Tran | |
| 9,222,787 B2 | 12/2015 | Blumenberg et al. | |
| 9,317,660 B2 | 4/2016 | Burich et al. | |
| 9,648,108 B2 | 5/2017 | Granqvist et al. | |
| 9,665,873 B2 | 5/2017 | Ackland et al. | |
| 9,829,331 B2 | 11/2017 | McBride et al. | |
| 9,830,516 B1 | 11/2017 | Biswas et al. | |
| 9,907,473 B2 | 3/2018 | Tran | |
| 9,923,973 B2 | 3/2018 | Granqvist et al. | |
| 10,234,290 B2 | 3/2019 | Lush et al. | |
| 10,244,948 B2 | 4/2019 | Pham et al. | |
| 10,327,673 B2 | 6/2019 | Eriksson et al. | |
| 10,415,990 B2 | 9/2019 | Cho et al. | |
| 10,433,768 B2 | 10/2019 | Eriksson et al. | |
| 10,515,990 B2 | 12/2019 | Hung et al. | |
| 10,634,511 B2 | 4/2020 | McBride et al. | |
| 10,816,671 B2 * | 10/2020 | Graham | G06Q 50/12 |
| 2003/0038831 A1 | 2/2003 | Engelfriet | |
| 2003/0109287 A1 | 6/2003 | Villaret | |
| 2005/0070809 A1 | 3/2005 | Acres | |
| 2005/0086405 A1 | 4/2005 | Kobayashi et al. | |
| 2006/0068812 A1 | 3/2006 | Carro et al. | |
| 2006/0136173 A1 | 6/2006 | Case, Jr. et al. | |
| 2006/0255963 A1 | 11/2006 | Thompson et al. | |
| 2007/0156335 A1 | 7/2007 | McBride et al. | |
| 2007/0208544 A1 | 9/2007 | Kulach et al. | |
| 2007/0276200 A1 | 11/2007 | Ahola et al. | |
| 2008/0052493 A1 | 2/2008 | Chang | |
| 2008/0109158 A1 | 5/2008 | Huhtala et al. | |
| 2008/0136620 A1 | 6/2008 | Lee et al. | |
| 2008/0158117 A1 | 7/2008 | Wong et al. | |
| 2008/0214360 A1 | 9/2008 | Stirling et al. | |
| 2008/0294663 A1 | 11/2008 | Heinley et al. | |
| 2008/0318598 A1 | 12/2008 | Fry | |
| 2009/0047645 A1 | 2/2009 | Dibenedetto et al. | |
| 2009/0048070 A1 | 2/2009 | Vincent et al. | |
| 2009/0094557 A1 | 4/2009 | Howard | |
| 2009/0100332 A1 | 4/2009 | Kanjilal et al. | |
| 2009/0265623 A1 | 10/2009 | Kho et al. | |
| 2010/0099539 A1 | 4/2010 | Haataja et al. | |
| 2010/0167712 A1 | 7/2010 | Stallings et al. | |
| 2010/0187074 A1 | 7/2010 | Manni | |
| 2010/0257014 A1 | 10/2010 | Roberts et al. | |
| 2010/0313042 A1 | 12/2010 | Shuster | |
| 2011/0010704 A1 | 1/2011 | Jeon et al. | |
| 2011/0152695 A1 | 6/2011 | Granqvist et al. | |
| 2011/0218385 A1 | 9/2011 | Bolyard et al. | |
| 2011/0251822 A1 | 10/2011 | Darley et al. | |
| 2011/0252351 A1 | 10/2011 | Sikora et al. | |
| 2011/0281687 A1 * | 11/2011 | Gilley | G06F 19/3475 |
| | | | 482/8 |
| 2011/0283224 A1 | 11/2011 | Ramsey et al. | |
| 2011/0288381 A1 * | 11/2011 | Bartholomew | A61B 5/024 |
| | | | 600/301 |
| 2011/0296312 A1 | 12/2011 | Boyer et al. | |
| 2011/0307723 A1 | 12/2011 | Cupps et al. | |
| 2012/0022336 A1 | 1/2012 | Teixeira | |
| 2012/0100895 A1 | 4/2012 | Priyantha et al. | |
| 2012/0109518 A1 | 5/2012 | Huang | |
| 2012/0116548 A1 | 5/2012 | Goree et al. | |
| 2012/0123806 A1 | 5/2012 | Schumann et al. | |
| 2012/0158289 A1 | 6/2012 | Bernheim Brush et al. | |
| 2012/0185268 A1 | 7/2012 | Wiesner et al. | |
| 2012/0219186 A1 | 8/2012 | Wang et al. | |
| 2012/0239173 A1 | 9/2012 | Laikari et al. | |
| 2012/0283855 A1 | 11/2012 | Hoffman et al. | |
| 2012/0289791 A1 * | 11/2012 | Jain | A61B 5/4848 |
| | | | 600/301 |
| 2012/0317520 A1 | 12/2012 | Lee | |
| 2013/0053990 A1 | 2/2013 | Ackland et al. | |
| 2013/0060167 A1 | 3/2013 | Dracup et al. | |
| 2013/0095459 A1 | 4/2013 | Tran | |
| 2013/0127636 A1 | 5/2013 | Aryanpur et al. | |
| 2013/0151874 A1 | 6/2013 | Parks et al. | |
| 2013/0178334 A1 | 7/2013 | Brammer | |
| 2013/0187789 A1 | 7/2013 | Lowe et al. | |

(56) References Cited

U.S. PATENT DOCUMENTS

| | | |
|---|---|---|
| 2013/0190903 A1 | 7/2013 | Balakrishnan et al. |
| 2013/0217979 A1 | 8/2013 | Blackadar et al. |
| 2013/0225370 A1 | 8/2013 | Flynt et al. |
| 2013/0234924 A1 | 9/2013 | Janefalkar et al. |
| 2013/0250845 A1 | 9/2013 | Greene et al. |
| 2013/0289932 A1 | 10/2013 | Baechler et al. |
| 2013/0304377 A1 | 11/2013 | Van Hende |
| 2013/0312043 A1 | 11/2013 | Stone et al. |
| 2013/0332286 A1 | 12/2013 | Medelius et al. |
| 2013/0345978 A1 | 12/2013 | Lush et al. |
| 2014/0018686 A1 | 1/2014 | Medelius et al. |
| 2014/0046223 A1 | 2/2014 | Kahn et al. |
| 2014/0094200 A1 | 4/2014 | Schatzberg et al. |
| 2014/0135593 A1* | 5/2014 | Jayalth .................. A61B 5/296 600/301 |
| 2014/0142732 A1 | 5/2014 | Karvonen |
| 2014/0149754 A1 | 5/2014 | Silva et al. |
| 2014/0159915 A1 | 6/2014 | Hong et al. |
| 2014/0163927 A1 | 6/2014 | Molettiere et al. |
| 2014/0208333 A1 | 7/2014 | Beals et al. |
| 2014/0218281 A1 | 8/2014 | Amayeh et al. |
| 2014/0235166 A1 | 8/2014 | Molettiere et al. |
| 2014/0237028 A1 | 8/2014 | Messenger et al. |
| 2014/0257533 A1 | 9/2014 | Morris et al. |
| 2014/0275821 A1 | 9/2014 | Beckman |
| 2014/0288680 A1 | 9/2014 | Hoffman et al. |
| 2014/0336796 A1* | 11/2014 | Agnew .................. G09B 5/06 700/91 |
| 2014/0337036 A1 | 11/2014 | Haiut et al. |
| 2014/0337450 A1 | 11/2014 | Fitbit |
| 2014/0343380 A1 | 11/2014 | Carter et al. |
| 2014/0350883 A1 | 11/2014 | Carter et al. |
| 2014/0365107 A1 | 12/2014 | Dutta et al. |
| 2014/0372064 A1 | 12/2014 | Darley et al. |
| 2015/0006617 A1 | 1/2015 | Yoo et al. |
| 2015/0037771 A1 | 2/2015 | Kaleal, III et al. |
| 2015/0042468 A1 | 2/2015 | White et al. |
| 2015/0057945 A1 | 2/2015 | White et al. |
| 2015/0113417 A1 | 4/2015 | Yuen et al. |
| 2015/0119198 A1 | 4/2015 | Wisbey et al. |
| 2015/0127966 A1 | 5/2015 | Ma et al. |
| 2015/0141873 A1 | 5/2015 | Fei |
| 2015/0160026 A1 | 6/2015 | Kitchel |
| 2015/0180842 A1 | 6/2015 | Panther |
| 2015/0185815 A1 | 7/2015 | Debates et al. |
| 2015/0209615 A1 | 7/2015 | Edwards |
| 2015/0233595 A1 | 8/2015 | Fadell et al. |
| 2015/0272483 A1 | 10/2015 | Etemad et al. |
| 2015/0312857 A1 | 10/2015 | Kim et al. |
| 2015/0317801 A1* | 11/2015 | Bentley ................ G08B 21/043 382/107 |
| 2015/0326709 A1 | 11/2015 | Pennanen et al. |
| 2015/0334772 A1 | 11/2015 | Wong et al. |
| 2015/0335978 A1 | 11/2015 | Syed et al. |
| 2015/0342533 A1 | 12/2015 | Kelner |
| 2015/0347983 A1 | 12/2015 | Jon et al. |
| 2015/0350822 A1 | 12/2015 | Xiao et al. |
| 2015/0362519 A1 | 12/2015 | Balakrishnan et al. |
| 2015/0374279 A1 | 12/2015 | Takakura et al. |
| 2015/0382150 A1* | 12/2015 | Ansermet .............. A61B 5/112 455/41.1 |
| 2016/0007288 A1 | 1/2016 | Samardzija et al. |
| 2016/0007934 A1 | 1/2016 | Arnold et al. |
| 2016/0012294 A1* | 1/2016 | Bouck ................ G06K 9/00348 345/158 |
| 2016/0023043 A1 | 1/2016 | Grundy |
| 2016/0026236 A1 | 1/2016 | Vasistha et al. |
| 2016/0034043 A1 | 2/2016 | Le Grand et al. |
| 2016/0034133 A1 | 2/2016 | Wilson et al. |
| 2016/0041593 A1 | 2/2016 | Dharawat |
| 2016/0058367 A1 | 3/2016 | Raghuram et al. |
| 2016/0058372 A1 | 3/2016 | Raghuram et al. |
| 2016/0059079 A1 | 3/2016 | Watterson |
| 2016/0072557 A1 | 3/2016 | Ahola |
| 2016/0081028 A1 | 3/2016 | Chang et al. |
| 2016/0081625 A1 | 3/2016 | Kim et al. |
| 2016/0084869 A1 | 3/2016 | Yuen et al. |
| 2016/0091980 A1 | 3/2016 | Baranski et al. |
| 2016/0104377 A1 | 4/2016 | French et al. |
| 2016/0135698 A1 | 5/2016 | Baxi et al. |
| 2016/0143579 A1 | 5/2016 | Martikka |
| 2016/0144236 A1* | 5/2016 | Ko .................... A63B 24/0075 434/247 |
| 2016/0148396 A1 | 5/2016 | Bayne et al. |
| 2016/0148615 A1 | 5/2016 | Lee et al. |
| 2016/0184686 A1 | 6/2016 | Sampathkumaran |
| 2016/0209907 A1 | 7/2016 | Han et al. |
| 2016/0226945 A1 | 8/2016 | Granqvist et al. |
| 2016/0259495 A1 | 9/2016 | Butcher et al. |
| 2016/0317097 A1 | 11/2016 | Adams et al. |
| 2016/0327915 A1 | 11/2016 | Katzer et al. |
| 2016/0328991 A1 | 11/2016 | Simpson et al. |
| 2016/0346611 A1 | 12/2016 | Rowley et al. |
| 2016/0367202 A1* | 12/2016 | Carter .................. A61B 5/6829 |
| 2016/0374566 A1 | 12/2016 | Fung et al. |
| 2016/0379547 A1 | 12/2016 | Okada |
| 2017/0010677 A1 | 1/2017 | Roh et al. |
| 2017/0011089 A1 | 1/2017 | Bermudez et al. |
| 2017/0011210 A1 | 1/2017 | Cheong et al. |
| 2017/0032256 A1 | 2/2017 | Otto et al. |
| 2017/0038740 A1 | 2/2017 | Knappe et al. |
| 2017/0063475 A1 | 3/2017 | Feng |
| 2017/0065230 A1 | 3/2017 | Sinha et al. |
| 2017/0087431 A1 | 3/2017 | Syed et al. |
| 2017/0124517 A1 | 5/2017 | Martin |
| 2017/0153119 A1 | 6/2017 | Nieminen et al. |
| 2017/0153693 A1 | 6/2017 | Duale et al. |
| 2017/0154270 A1 | 6/2017 | Lindman et al. |
| 2017/0168555 A1 | 6/2017 | Munoz et al. |
| 2017/0173391 A1 | 6/2017 | Wiebe et al. |
| 2017/0232294 A1 | 8/2017 | Kruger et al. |
| 2017/0262699 A1 | 9/2017 | White et al. |
| 2017/0266494 A1 | 9/2017 | Crankson et al. |
| 2017/0316182 A1 | 11/2017 | Blackadar et al. |
| 2017/0340221 A1 | 11/2017 | Cronin et al. |
| 2018/0015329 A1 | 1/2018 | Burich et al. |
| 2018/0108323 A1 | 4/2018 | Lindman et al. |
| 2018/0193695 A1 | 7/2018 | Lee |
| 2018/0345077 A1 | 12/2018 | Blahnik et al. |
| 2019/0025928 A1 | 1/2019 | Pantelopoulos et al. |
| 2019/0056777 A1 | 2/2019 | Munoz et al. |
| 2019/0069244 A1 | 2/2019 | Jeon et al. |
| 2019/0367143 A1 | 12/2019 | Sinclair et al. |

FOREIGN PATENT DOCUMENTS

| | | |
|---|---|---|
| CN | 102495756 A | 6/2012 |
| CN | 103309428 A | 9/2013 |
| CN | 103631359 A | 3/2014 |
| CN | 204121706 U | 1/2015 |
| CN | 104680046 A1 | 6/2015 |
| CN | 105242779 A1 | 1/2016 |
| CN | 106062661 A | 10/2016 |
| CN | 106604369 A | 4/2017 |
| CN | 108052272 A | 5/2018 |
| CN | 103154954 B | 6/2018 |
| CN | 108377264 A | 8/2018 |
| CN | 108983873 A | 12/2018 |
| EP | 1755098 A2 | 2/2007 |
| EP | 2107837 A1 | 10/2009 |
| EP | 2172249 A2 | 4/2010 |
| EP | 2770454 A1 | 8/2014 |
| EP | 2703945 A2 | 3/2015 |
| EP | 2849473 A1 | 3/2015 |
| EP | 2910901 A1 | 8/2015 |
| EP | 2996409 A1 | 3/2016 |
| EP | 3018582 A2 | 5/2016 |
| EP | 3023859 A1 | 5/2016 |
| EP | 3361370 A | 8/2018 |
| ER | 2096820 A1 | 9/2009 |
| FI | 126911 B | 2/2017 |
| GB | 2404593 A | 2/2005 |
| GB | 2425180 A | 10/2006 |

(56) References Cited

FOREIGN PATENT DOCUMENTS

| | | | |
|---|---|---|---|
| GB | 2513585 | A | 11/2014 |
| GB | 2530196 | A | 3/2016 |
| GB | 2537423 | A | 10/2016 |
| GB | 2541234 | A | 2/2017 |
| GB | 2555107 | A | 4/2018 |
| KR | 20110070049 | A | 6/2011 |
| KR | 101500662 | B1 | 3/2015 |
| SE | 528295 | C2 | 10/2006 |
| TW | 201706840 | A | 2/2017 |
| TW | I598076 | A | 9/2018 |
| WO | WO02054157 | A1 | 7/2002 |
| WO | WO2010083562 | A1 | 7/2010 |
| WO | WO2010144720 | A1 | 12/2010 |
| WO | WO2011061412 | A1 | 5/2011 |
| WO | WO2011123932 | A1 | 10/2011 |
| WO | WO2012037637 | A1 | 3/2012 |
| WO | WO2012115943 | A1 | 8/2012 |
| WO | WO2012141827 | A2 | 10/2012 |
| WO | WO2013091135 | A1 | 6/2013 |
| WO | WO2013121325 | A2 | 8/2013 |
| WO | WO2014118767 | A1 | 8/2014 |
| WO | WO2014144258 | A2 | 9/2014 |
| WO | WO2014193672 | A1 | 12/2014 |
| WO | WO2014209697 | A1 | 12/2014 |
| WO | WO2015021407 | A1 | 2/2015 |
| WO | WO2014182162 | A3 | 6/2015 |
| WO | WO2015087164 | A1 | 6/2015 |
| WO | WO2015131065 | A1 | 9/2015 |
| WO | WO2016022203 | A1 | 2/2016 |
| WO | WO2017011818 | A1 | 1/2017 |
| WO | WO2018217348 | A1 | 11/2018 |
| WO | WO2018222936 | A1 | 12/2018 |

OTHER PUBLICATIONS

Qualcomm Snapdragon Wear 3100 Platform Supports New Ultra-Low Power System Architecture For Next Generation Smartwatches. Qualcomm Technologies, Inc., Sep. 10, 2018, Retrieved on May 28, 2020 from: <https://www.qualcomm.com/news/releases/2018/09/10/qualcomm-snapdragon-wear-3100-platform-supports sections "Snapdragon Wear 3100 Based Smartwatches Aim to Enrich the User Experience" on pp. 3-4.
CNET: Dec. 11, 2017, "Apple watch can now sync with a treadmill", youtube.com, [online], Available from: https://www.youtube.com/watch?v=7RvMC3wFDME [ Accessed Nov. 19, 2020].
Sieber et al: Embedded systems in the Poseidon MK6 rebreather. Intelligent Solutions in Embedded Systems, 2009, pp. 37-42.
CASH: A guide to GPS and route plotting for cyclists. 2018. www.cyclinguk.org/article/guide-gps-and-route-plotting-cyclists.
Sheta et al: Packet scheduling in LTE mobile network. International Journal of Scientific & Engineering Research, Jun. 2013, vol. 4, Issue 6.

* cited by examiner

FIG. 7

ENGAGING EXERCISING DEVICES WITH A MOBILE DEVICE

RELATED APPLICATIONS

This application is a Continuation-in-Part of U.S. patent application Ser. No. 15/382,763, filed on Dec. 19, 2016, which claims priority to Finnish Patent Application No. 20155989, filed on Dec. 21, 2015. The subject matter of which are incorporated by reference in their entirety. Additionally, the subject matter of U.S. patent application Ser. No. 14/945,914 is herein incorporated by reference in its entirety.

FIELD

The present invention relates to an apparatus comprising at least one processing core and at least one memory including computer program code.

Further, the present invention relates to an use of an apparatus in connection with an exercising device and a mobile device.

Furthermore, the present invention relates to an arrangement comprising an apparatus, an exercising device and a mobile device.

BACKGROUND

Different exercising devices such as ergometers, gym exercising devices, fitness devices, sports devices, weight lifting devices, exercise bikes, treadmills, rowing machines, cross trainers, etc. are known. Some of the known exercising devices are often equipped with an internal display, a user interface and/or a memory, for example exercise bikes or treadmills. Further, various mobile devices are known by means of which information can be stored, processed and/or displayed. The mobile devices typically comprise a user interface such as a touchscreen, a keyboard or at least one button. Examples of such devices are smartphones, tablets, smartwatches and wrist-watches.

User sessions, such as training sessions, may be recorded, for example in notebooks, spreadsheets or other suitable media. Recorded training sessions enable more systematic training, and progress toward set goals can be assessed and tracked from the records so produced. Such records may be stored for future reference, for example to assess progress an individual is making as a result of the training. An activity session may comprise a training session or another kind of session.

Personal devices, such as, for example, smart watches, smartphones or smart jewelry, may be configured to produce recorded sessions of user activity. Such recorded sessions may be useful in managing physical training, child safety or in professional uses. Recorded sessions, or more generally sensor-based activity management, may be of varying type, such as, for example, running, walking, skiing, canoeing, wandering, or assisting the elderly.

Recorded sessions may be viewed using a personal computer, for example, wherein recordings may be copied from a personal device to the personal computer. Files on a personal computer may be protected using passwords and/or encryption, for example.

Personal devices may be furnished with sensors, which may be used, for example, in determining a heart-beat rate of a user during a user session. A recorded heart-beat rate of a user may be later observed using a personal computer, for example.

Document FI 20155989 discloses an apparatus comprising a memory configured to store first-type sensor data, at least one processing core configured to compile a message based at least partly on the first-type sensor data, to cause the message to be transmitted from the apparatus, to cause receiving in the apparatus of a machine readable instruction, and to derive an estimated activity type, using the machine readable instruction, based at least partly on sensor data.

SUMMARY OF THE INVENTION

The invention is defined by the features of the independent claims. Some specific embodiments are defined in the dependent claims.

According to a first aspect of the present invention, there is provided an apparatus comprising at least one processing core, at least one memory including computer program code, the at least one memory and the computer program code being configured to, with the at least one processing core, cause the apparatus at least to receive a first sensor data stream from an exercising device, receive a second sensor data stream from a mobile device, correlate the first data stream with the second data stream, determine that the exercising device is engaged with the mobile device, and provide indication to the exercising device and the mobile device that the devices are engaged with each other.

Various embodiments of the first aspect may comprise at least one feature from the following bulleted list:

- the apparatus is configured to store and process sensor data received from the exercising device
- the apparatus is configured to store and process sensor data received from the mobile device
- the first sensor data stream is based on a first acceleration sensor and the second data stream is based on a second acceleration sensor
- the first sensor data stream is based on a first angular velocity sensor and the second data stream is based on a second angular velocity sensor
- the apparatus is a server or a server infrastructure
- the apparatus is configured to receive the first sensor data stream from an ergometer, a gym exercising device, a fitness device, a sports device, a weight lifting device, an exercise bike, a treadmill, a rowing machine, or a cross trainer
- the apparatus is configured to receive the second sensor data stream from a wrist-watch, a tablet, a smartwatch, a smartphone, a wearable sensor or any other external sensor
- the apparatus is configured to receive a third sensor data stream from a wearable sensor or an external sensor
- the apparatus is capable of storing at least a part of the data streams in a memory
- time stamps associated with sensor data are contained in each of the data streams
- the processing core is capable of arranging sensor data in an order depending on the time stamps associated with the sensor data
- the apparatus is capable of estimating a start and an end of an activity type based on sensor data and the associated time stamps
- the apparatus is configured to allow a user to remotely read-out at least a part of at least one of the first sensor data stream, the second sensor data stream and the third data stream
- the apparatus is remotely accessible by a person in order to analyse a user session the apparatus is configured to estimate an activity type of a user based on the correlated data streams According to a second aspect of the present invention, there is provided a use of the apparatus according to at least one of claims 1-13 in connection with an exercising device and a mobile device. According to an embodiment, the use takes place in a gym, in connection with a training session, in connection with a sports session or in connection with a fitness session.

According to a third aspect of the present invention, there is provided an arrangement comprising an apparatus according to at least one of claims 1-13, an exercising device and a mobile device.

Various embodiments of the third aspect may comprise at least one feature from the following bulleted list:
- the exercising device is enabled to act as a server having control over the user interface of the mobile device
- the exercising device is configured to participate in pairing with the mobile device
- the exercising device is configured to participate in pairing with the mobile device during a session with the exercising device
- the exercising device is configured to transmit program code to be stored and processed by the mobile device after a pairing process
- the exercising device is capable of transmitting parameters and/or logics to the mobile device after a pairing process
- the exercising device is capable of transmitting instructions to the mobile device after a pairing process
- the exercising device is capable of receiving data which has been input via a user interface of the mobile device after a pairing process
- the exercising device is capable of transmitting a recipe or an instruction to the mobile device how to analyse movements of a user
- the recipe can be retrieved from a server by at least one of the mobile device, the apparatus, or the exercising device
- the exercising device is configured to transmit data to the mobile device after a pairing process, which data is to be displayed on a display of the mobile device.
- the exercising device is configured to transmit sensor data to the mobile device and to receive in response input parameters from the mobile device after a pairing process
- the exercising device is an ergometer, a gym exercising device, a fitness device, a sports device, a weight lifting device, an exercise bike, a treadmill, a rowing machine, or a cross trainers
- the exercising device is configured to transmit data to a server
- the exercising device is capable of transmitting and receiving signals wirelessly
- the exercising device is configured to transmit sensor data and associated time stamps to at least one of the apparatus and the mobile device
- the mobile device is enabled to act as a client whose content is fully or at least partially controlled by the exercising device
- the mobile device is configured to participate in pairing with the exercising device
- the mobile device is configured to participate in pairing with the exercising device during a session with the exercising device
- the mobile device is configured to store and process program code received from the exercising device after a pairing process
- the mobile device is capable of receiving parameters and/or logics from the exercising device after a pairing process
- the mobile is capable of processing instructions received from the exercising device after a pairing process
- the mobile device is capable of starting calculations based on the received instructions after a pairing process
- the mobile device is capable of starting user interface methods based on the received instructions after a pairing process
- the mobile device is capable of receiving a recipe or instruction from the exercising device how to analyse movements of a user after a pairing process
- the mobile device is configured to control parameters or functions of the exercising device
- the mobile device is capable of controlling a music program or a music playlist stored in the memory of the exercising device or in the memory of a second mobile device such as a tablet or a smartphone
- the mobile device is configured to serve as a display of the exercising device after a pairing process
- the mobile device is configured to serve as an additional display of the exercising device after a pairing process
- the mobile device is configured to serve as a user interface of the exercising device after a pairing process
- the mobile device is configured to serve as an additional user interface of the exercising device after a pairing process
- the mobile device is configured to serve as a memory of the exercising device after a pairing process
- the mobile device is configured to serve as an additional memory of the exercising device after a pairing process
- the mobile device is configured to participate in the pairing process during a session with the exercising device after a pairing process
- the session is based on sensors of the mobile device and the exercising device
- the mobile device is configured to receive sensor data from the exercising device and to transmit in response input parameters to the exercising device after a pairing process
- the mobile device is capable of transmitting instructions to the exercising device, for example to change a speed of a part of the exercising device, to change a resistance of the exercising device, or to change a weight of the exercising device after a pairing process
- the mobile device is configured to transmit data to a server
- the mobile device is capable of transmitting and receiving signals wirelessly
- the mobile device is configured to transmit sensor data and associated time stamps to at least one of the apparatus and the exercising device
- the mobile device is a wrist-watch, a tablet, a smartwatch or a smartphone Considerable advantages are obtained by means of certain embodiments of the present invention. An apparatus comprising at least one processing core and at least one memory including computer program code is provided. According to certain embodiments of the present invention, it can be determined that an exercising device and a mobile device are engaged with each other based on correlated sensor data streams received from the exercising device and the mobile device. An activity type of a user can be estimated by the apparatus based on the received sensor data streams of the exercising device and the mobile device. The apparatus can be remotely accessible by a person in order to analyse a user session in real time or at a later stage. For example, the apparatus may be connected with the internet. A client connected to the apparatus may receive the sensor data streams and may be configured to cause pairing of the mobile device and the exercising device based on the correlated data streams or based on instructions input by a person.

After providing indication to the exercising device and the mobile device that the devices are engaged with each other, the exercising device can participate in pairing with the mobile device and the mobile device can participate in pairing with the exercising device according to certain embodiments of the present invention. The mobile device and the exercising can form at least temporarily a unit in which the mobile device serves as a display, a user interface and/or a memory of the exercising device. According to certain embodiments of the present invention, the mobile device serves as a display of the exercising device. The mobile device may serve as the only display or as an additional display of the exercising device during the time period of a user session. According to certain other embodiments of the present invention, the mobile device serves as a user interface of the exercising device. The mobile device may serve as the only user interface or as an additional user interface of the exercising device during the time period of a user session.

A mobile device and the exercising device can temporarily form a unit during the time period of a user session, a training session or a sports session. According to an embodiment, an app which is related to a specific exercising device can be stored in the memory of the mobile device of a user. Settings of the app can be personalized. For example, when the user is bringing his/her mobile device to a gym, the user can start a user session using his/her own personalized settings. Personalized settings may include information about age, weight, height, gender, body mass index, maximum performance capacity, activity parameter, previous energy expenditure and maximum heart rate, for instance. Also personalized exercise-guidance parameters such as an energy expenditure target, heart rate zones, activity zones, anaerobic threshold, fitness classification identifier and/or dehydration warning limits may be stored on the mobile device. Personalized data determined by sensors of the exercising device can further be stored in the memory of the mobile device and/or in the internet. Further, personalized data determined by sensors of the mobile device can be stored in the memory of the mobile device and/or in the internet. Determined data of the user, for example movement data or heart-beat rate data, can then be analysed at a later stage subsequent to the user session, training session or sports session. When another user is using the exercising device in the gym, his/her mobile device and the exercising device temporarily form a unit during the time period of another user session. Personalized settings can be used by this other user and personalized data can be stored in the memory of the respective mobile device and/or in the internet for further analysis. Consequently, it is not necessary to store any personalized data on the memory of the exercising device according to certain embodiments of the present invention.

According to another embodiment, no program code or a minimum amount thereof needs to be installed on the mobile device such as a wrist watch. The mobile device serves as a display and/or user interface for the exercising device. The procedure is controlled by the exercising device or the apparatus. Minimum system requirements are required for the mobile device. According to this embodiment, the input data is processed by the exercising device or the apparatus. The bidirectional communication link between the mobile device and the exercising device or apparatus may be used to enable the exercising device or apparatus to act as a server having control over the user interface and the mobile device to act as a client whose content is fully or at least partially controlled by the exercising device or apparatus.

Receiving a first sensor data stream from the exercising device, receiving a second sensor data stream from the mobile device, correlating the first data stream with the second data stream, determining that the exercising device is engaged with the mobile device, and providing indication to the exercising device and the mobile device that the devices are engaged with each other can take place automatically, thus providing to the user a comfortable user experience.

According to certain embodiments, a temporarily combined unit can share a classification task. I.e. the exercising device has its own classification task to produce semantic events like 'lift', 'release', 'step' etc. Similarly, the mobile device has its own classification task to produce semantic events. The system creates a more comprehensive analysis of the user's actions to provide e.g. a deeper understanding of the user's biomechanical accuracy.

Certain embodiments of the present invention are applicable with regards to health care, in industry, in working environments, in sports, and the like.

EMBODIMENTS

Figure 1:
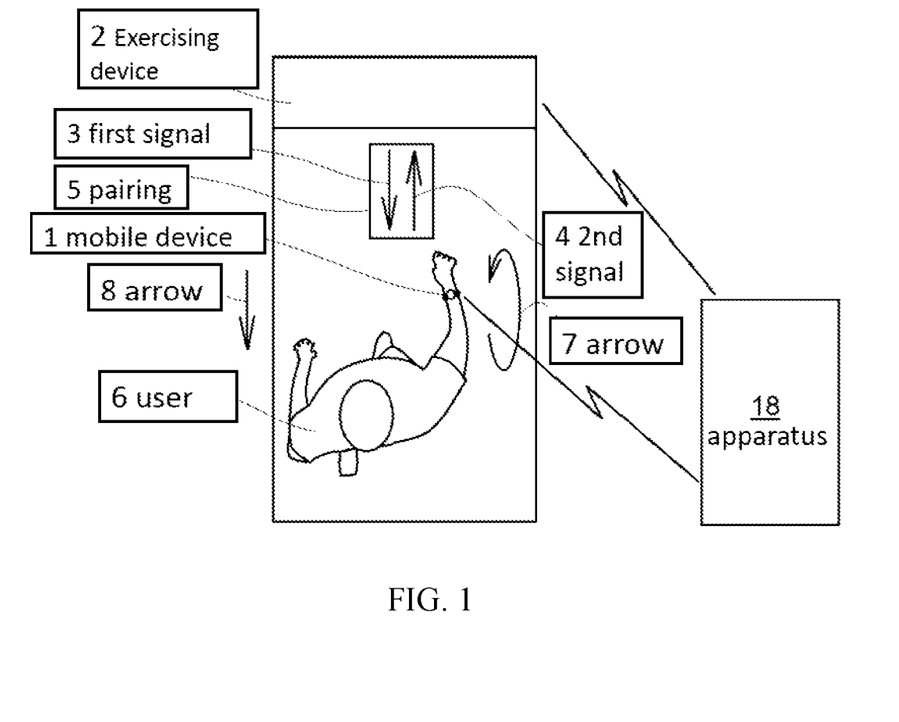
FIG. 1 illustrates a schematic top view of an apparatus in accordance with at least some embodiments of the present invention.

In FIG. 1 a schematic top view of an apparatus 18 in accordance with at least some embodiments of the present invention is illustrated. The apparatus 18 comprises at least one processing core and at least one memory including computer program code. The at least one memory and the computer program code are configured to, with the at least one processing core, cause the apparatus 18 at least to receive a first sensor data stream from an exercising device 2, receive a second sensor data stream from a mobile device 1, correlate the first data stream with the second data stream, determine that the exercising device 2 is engaged with the mobile device 1, and provide indication to the exercising device 2 and the mobile device 1 that the devices 1, 2 are engaged with each other. In other words, the apparatus 18 is capable of estimating that a user 6 is using a specific exercising device 2 by correlating sensor data received from the mobile device 1 and sensor data received from the exercising device 2. The apparatus 18 is capable of estimating an activity type of a user 6, for example running, based on the correlated data streams.

The mobile device 1 may be a wrist-watch, for instance. The exercising device 2 may be a treadmill, for instance. The apparatus 18 may be, for example, a server or server infrastructure. The apparatus 18 is configured to store and process sensor data received from the exercising device 2. Further, the apparatus 18 is configured to store and process sensor data received from the mobile device 2. Of course, the apparatus may be also configured to store and process sensor data received from a wearable sensor or any other external sensor, for example a MOVESENSE sensor. Such sensor data may be wirelessly transferred to the apparatus 18 directly or to at least one of the mobile device 1 and the exercising device 2 first and then to the apparatus 18.

According to a certain embodiment, an external sensor (not shown), for example a MOVESENSE sensor, is attached to a user and connected to the mobile device 1, for example a wrist watch 1. When the user comes to an exercising device 2, the mobile device 1 automatically displays information. Simultaneously, the mobile device 1 receives instructions from the exercising device 2 and/or apparatus 18. However, also the exercising device 2 and/or apparatus 18 may receive data from the mobile device 1 and/or the external sensor. The data may, for example, include personal data, sensor data and/or external sensor data. The data is typically processed by the exercising device 2 and/or apparatus 18. This kind of user experience is automatically created. When the user changes the exercising device 2, for example in a gym, the displayed information on the display of the mobile device 1 also automatically changes. The exercising device 2 can additionally receive further data from a server or via the internet. External sensor data can be analysed by the exercising device 2 and/or apparatus 18 and content, for example information derived from the sensor data, can be automatically displayed on the mobile device 1. In such a situation, the exercising device 2 may be used to enable the exercising device 2 to act as a server having control over the user interface and the mobile device 1 to act as a client whose content is fully or at least partially controlled by the exercising device 2

The first sensor data stream may be, for example, based on a first acceleration sensor and the second data stream may be, for example, based on a second acceleration sensor. I.e., the mobile device 1 comprises an acceleration sensor and the exercising device 2 comprises an acceleration sensor and the acceleration data of both sensors is received by the server 18. The mobile device 1 and the exercising device 2 both measure the same parameter, i.e. acceleration. The sensor of the mobile device 1 may, for example, measure acceleration of a cyclical motion of the right arm of the user as indicated by arrow 7. The sensor of the exercising device 2 may, for example, measure acceleration of the treadmill belt as indicated by arrow 8. According to other embodiments, the sensor of the mobile device 1 and the sensor of the exercising device 2 both measure another parameter, for example angular velocity.

After indication that the devices 1, 2 are engaged with each other has been provided to the exercising device 2 and the mobile device 1, the exercising device 2 may participate in pairing with the mobile device 1 and the mobile device 1 may participate in pairing with the exercising device 2. The mobile device 1 in the form of a wrist-watch comprises at least one processing core and at least one memory including computer program code. The at least one memory and the computer program code are configured to, with the at least one processing core, cause the mobile device 1 at least to receive a first signal 3 from an exercising device 2, process the received signal, respond to the received signal by transmitting a second signal 4 to the exercising device 2, and participate in a pairing process 5 with the exercise device 2. Further examples are described below in connection with FIG. 2 to FIG. 6.

According to certain embodiments, the apparatus 18 may be further configured to allow a user to remotely read-out at least a part of at least one of the first sensor data stream and the second sensor data stream. In other words, the apparatus 18 is remotely accessible by a person in order to analyse a user session.

The first sensor data stream may be received by the apparatus 18 from the exercising device 2 via wire or a wireless technology, for example a low power wireless communication technology such as Bluetooth, Bluetooth Low Energy, or Wibree. The second sensor data stream may be typically received by the apparatus 18 from the mobile device 1 via a wireless technology, for example a low power wireless communication technology such as Bluetooth, Bluetooth Low Energy, or Wibree.

Figure 2:
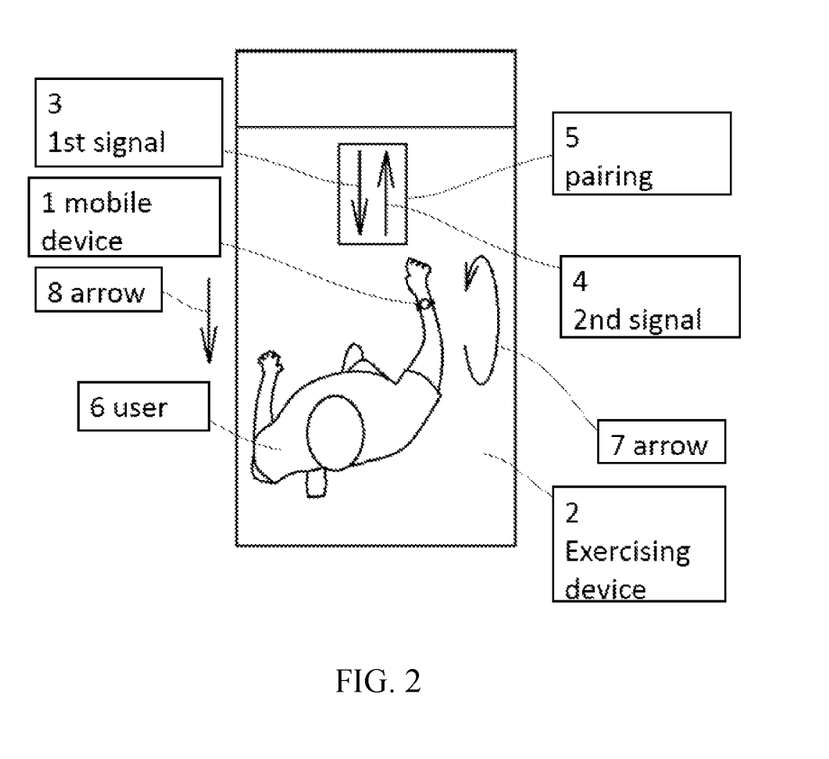
FIG. 2 illustrates a schematic top view of a mobile device comprised by an arrangement in accordance with at least some embodiments of the present invention.

In FIG. 2 a schematic top view of a mobile device 1 comprised by an arrangement in accordance with at least some embodiments of the present invention is illustrated. The shown mobile device 1 is a wrist-watch. The shown exercising device 2 is a treadmill. The mobile device 1 comprises at least one processing core and at least one memory including computer program code. The at least one memory and the computer program code are configured to, with the at least one processing core, cause the mobile device 1 at least to receive a first signal 3 from an exercising device 2, process the received signal, respond to the received signal by transmitting a second signal 4 to the exercising device 2, and participate in a pairing process 5 with the exercise device 2. Pairing in accordance with the present invention takes place after indication that the mobile devices 1 and the exercising device 2 are engaged with each other has been provided to the exercising device 2 and the mobile device 1 as described in connection with FIG. 1.

Sensor data contained in the data streams is typically associated with time stamps. For example, one acceleration value is measured every second and for each measured acceleration value the respective time is transmitted to the apparatus 18 in the form of a time stamp. Sensor data from the mobile device 1 having a first time stamp is compared with sensor data from the exercising device 2 having an identical time stamp. This procedure can be repeated for a plurality of second, third, etc. time stamps. When the sensor data from the mobile device and the sensor data from the exercising device correlate with each other, the apparatus is capable of determining that the exercising device 2 is engaged with the mobile device 1. When a user changes an exercising device, for example in a gym, pairing between the new exercising device and the mobile device can be automatically initiated based on the sensor data from the new exercising device correlating with the sensor data from the mobile device 1.

In other words, when a user 6 wearing the wrist-watch 1 starts to use the exercising device 2, sensor data streams are transmitted from the mobile device 1 and the exercising device 2 to the apparatus 18 in the form of a server. The server determines that the exercising device 2 is engaged with the mobile device 1 and estimates an activity type of the user, for example running. Subsequent to providing indication to the exercising device 2 and the mobile device 1 that the devices 1, 2 are engaged with each other, the wrist-watch 1 and the exercising device start to communicate with each other. A first signal as indicated by arrow 3 from the exercising device 2 is transmitted to the wrist-watch 1. Then the received signal 3 is processed by the processing core of the wrist-watch 1. Subsequently, a second signal as indicated by arrow 4 is transmitted from the wrist-watch 1 to the exercising device 2. This process is called pairing 5. Data between the wrist-watch 1 and the exercising device 2 can now be transferred between the wrist-watch 1 and the exercising device 2. Data is typically transferred using low power wireless communication technology such as Bluetooth, Bluetooth Low Energy, or Wibree.

The treadmill belt of the exercising device 2 may be moving with a specific speed as indicated by arrow 8 as a user 6 is running on the belt. At the same time, the arms of the runner 6 move cyclically as indicated by arrow 7. Data may be determined by the sensors of the wrist-watch 1. Examples of such determined data are a heart-beat rate, number of steps during a certain period of time, or acceleration data. Data may also be determined by sensors of the exercising device 2 and transmitted to the mobile device 1. An example of such data is the speed of the moving treadmill belt of the exercising device 2. The information about the speed of the treadmill belt may be transmitted from the exercising device 1 to the wrist-watch 1. The information about the speed of the treadmill belt may then be displayed on the wrist-watch. In other words, the wrist-watch 1 is configured to serve as a display of the exercising device 2. Of course, also data determined by at least one sensor of the wrist-watch 1 may be displayed on the display of the wrist-watch. The user 6 may further choose which data is displayed.

According to certain embodiments, the exercising device 2 may also comprise an additional display and data may be transmitted from the wrist-watch 1 to the exercising device 2. A user 6 may choose which information is shown on the display of the exercising device 2 and which information is at the same time displayed on the display of the wrist-watch 1. In other words, the user 6 may choose which sensor data is displayed on the display of the wrist-watch 1 and which sensor data is displayed on the display of the exercising device 2.

According to certain other embodiments, the mobile device 1 is configured to control parameters or functions of the exercising device 2 after the pairing process 5. In the shown example, a user 6 may control the speed of the treadmill belt of the exercising device 2 as indicated by arrow 8 via a user interface of the wrist-watch 1. A user interface of the wrist watch 1 may be a touchscreen or at least one button, for instance. User instructions to change the speed of the treadmill belt may be transmitted from the wrist-watch 1 to the exercising device 2 and processed by the exercising device 2, thus causing the exercising device 2 to change the speed of the treadmill belt. According to this embodiment, the procedure is typically controlled by the exercising device 2 such that no program code or a minimum amount thereof needs to be installed on the mobile device 1. The mobile device 1 serves as a user interface for the exercising device 2. In other words, a computer program comprising program instructions which, when loaded into the exercising device 2, cause e.g. graphical user interface data to be determined for the mobile device 1 is provided. The graphical user interface data is wirelessly transmitted to the mobile device 1 from the exercising device 2 to provide at least one user interface functionality on the mobile device 1. Then data corresponding to user input is received and wirelessly transmitted to the exercising device 2. Minimum system requirements such as processing capacity and memory capacity are required for the mobile device 1. According to this embodiment, the input data is completely or at least partially processed by the exercising device 2. The bidirectional communication link between the mobile device 1 and the exercising device 2 may be used to enable the exercising device 2 to act as a server having control over the user interface and the mobile device 1 to act as a client whose content is fully or at least partially controlled by the exercising device 2.

Figure 3:
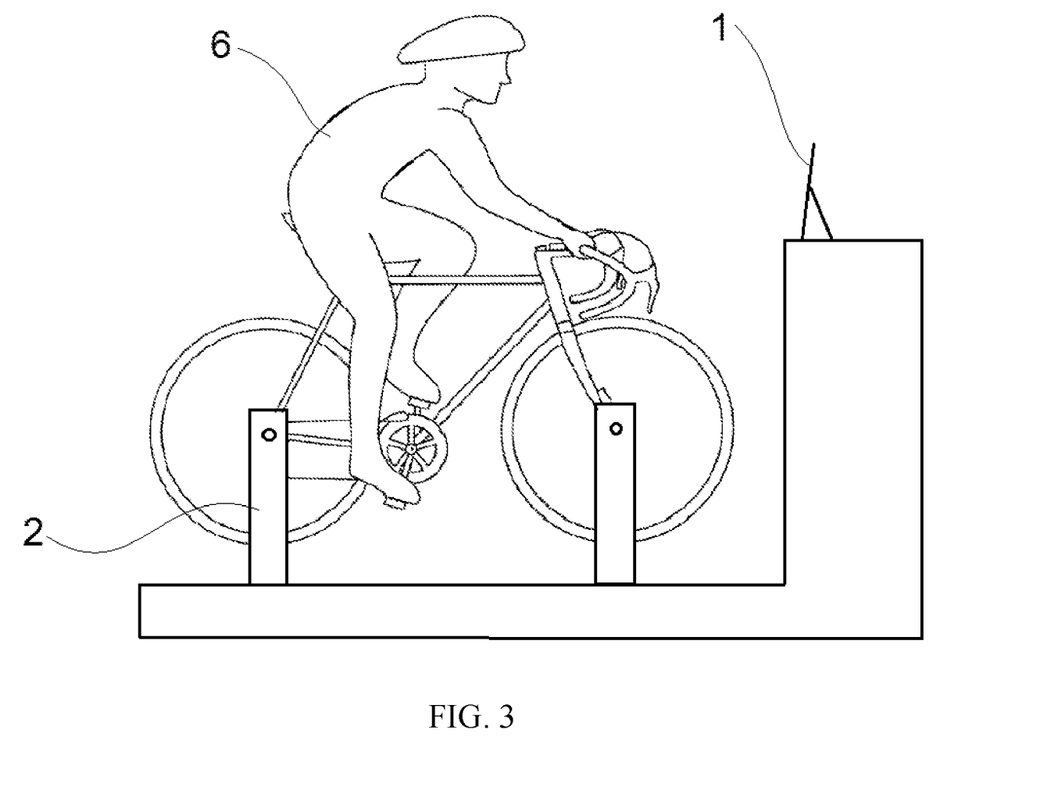
FIG. 3 illustrates a schematic side view of a mobile device comprised by another arrangement in accordance with at least some embodiments of the present invention.

In FIG. 3 a schematic side view of a mobile device 1 comprised by another arrangement in accordance with at least some embodiments of the present invention is illustrated. The shown mobile device 1 may be a tablet or other mobile device. The shown exercising device 2 is an ergometer or indoor exercise bike. Prior to pairing, indication that the mobile devices 1 and the exercising device 2 are engaged with each other has been provided to the exercising device 2 and the mobile device 1. After the pairing process as described above in connection with FIG. 2, parameters and/or logics such as an app are transmitted from the exercising device 2 to the mobile device 1. The mobile device 1 is configured to store and process program code received from the exercising device 2. The mobile device 1 is configured to serve as a display of the exercising device 2.

For example, a video simulation of a cycling track may be displayed on the display of the mobile device 1. Thus, the user 6 can cycle along the simulated track. Sensors of the exercising device 2 may determine the cycling speed of the user 6, for example. The sensor data of the exercising device 2 is then transmitted to the mobile device 1. The sensor data can be used as input data for the video simulation displayed on the mobile device 1. In other words, the user 6 can cycle along the virtual track with varying speeds. The visualization of the virtual cycling simulation is calculated based on the speed data obtained from the sensor data of the exercising device 2. On the other side, data may be transmitted from the mobile device 1 to the exercising device 2, thus causing the exercising device to change a parameter. Altitude data along the virtual track stored in the app may be provided, for instance. The altitude data can be used as input data for the parameters of the exercising device 2 as a function of time. When the data is received by the exercising device 2, it causes the exercising device 2 to change the resistance of the exercise bike during cycling along the virtual track. In other words, cycling upwards or downwards along the virtual track can be simulated. The exercising device 2 is configured to transmit sensor data to the mobile device 1 and to receive in response input parameters from the mobile device 1. Consequently, cycling along a virtual track, for example a passage of the Tour de France, can be simulated.

The exercising device 2 may be, for example, located in a gym and different users may subsequently cycle along the virtual track. When each user bring his/her own mobile device 1 to the gym, for each user a period of time may be determined by the app for cycling from the beginning of the virtual track to the end of the virtual track. The period of time for each user may then be transmitted from the respective mobile device 1 to the exercising device 2 and stored in a memory of the exercising device 2. The different periods of time may be ranked and listed so that a user can see his/her results in comparison to the results of other users. Thus, it is possible to simulate a cycling competition, for instance.

Of course, the mobile device 1 may also be used for displaying only information such as cycling speed, length of cycling session period or for selecting a cycling resistance of the exercising device 2.

Data determined by sensors of the exercising device 2 may be received by and stored in the mobile device 1. Alternatively, data determined by sensors of the exercising device 2 may be received by the mobile device and stored in the cloud. Thus, the user 6 can analyse the stored data at a later stage by reading out the memory of the mobile device 1 or viewing a webpage in the internet.

Figure 4:
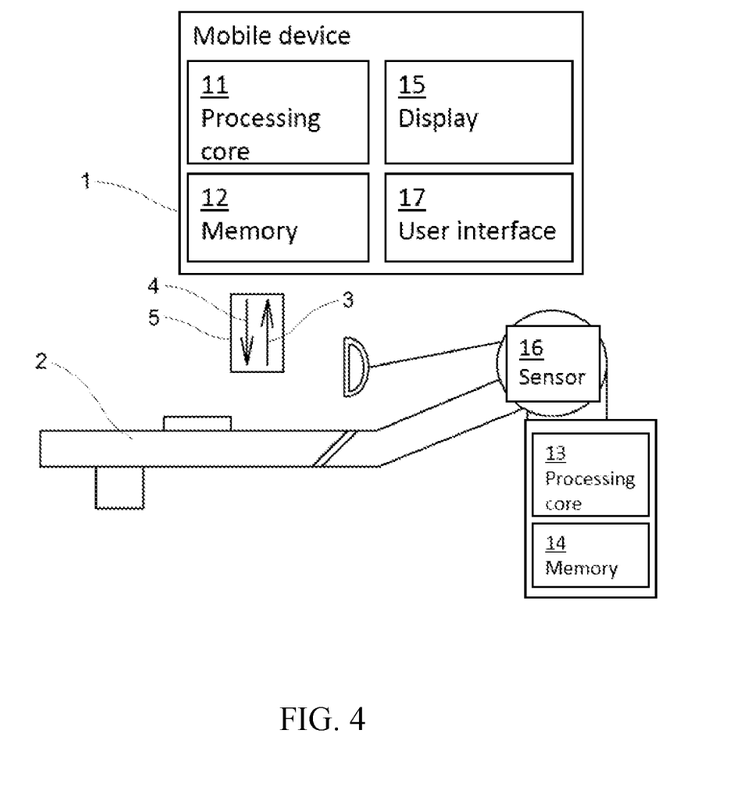
FIG. 4 illustrates a schematic side view of an exercising device comprised by a further arrangement in accordance with at least some embodiments of the present invention.

In FIG. 4 a schematic side view of an exercising device 2 comprised by a further arrangement in accordance with at least some embodiments of the present invention is illustrated. In the shown embodiment, the exercising device 2 is a rowing machine. The mobile device 1 may be a tablet computer, for instance. The exercising device 2 comprises at least one processing core 13 and at least one memory 14 including computer program code. The at least one memory 14 and the computer program code are configured to, with the at least one processing core 13, cause the exercising device 2 at least to transmit a first signal 3 to a mobile device 1, receive a second signal 4 from the mobile device 1, and participate in pairing 5 with the mobile device 1. Prior to pairing, indication that the mobile devices 1 and the exercising device 2 are engaged with each other has been provided to the exercising device 2 and the mobile device 1.

Subsequent to the pairing process 5, program code to be stored and processed by the mobile device 1 can be transmitted from the exercising device 2. Parameters and/or logics such as a rule engine, an app, a classification recipe or a html web page can be transmitted to the mobile device, for instance.

For example, an app may be transmitted to the mobile device 1. A user can select a training program with the help of the app. During the training session, the exercising device 2 may, for example, transmit a recipe or an instruction to the mobile device 1 how to analyse movements of a user 6. The movements of the user may be determined or recorded using sensors of the exercising device 2. Examples of such sensors of the exercising device are force sensors and acceleration sensors. Data determined by the sensors of the exercising device 2 may be shown on a display 15 of the mobile device 1.

A user can further input data using a user interface 17 of the mobile device 1. A user interface 17 may be, for example, a touchscreen, a button, a keyboard or an optical system analysing gestures of the user. The exercising device 2 is capable of receiving the data which has been input via the user interface 17 of the mobile device 1. The exercising device 2 is capable of receiving instructions from the mobile device 1. For example, another training program may be selected.

According to certain embodiments, a first exercising device 2 and a first mobile device 1 in accordance with at least some embodiments form a first unit and a second exercising device 2 and a second mobile device 1 in accordance with at least some embodiments form a second unit. The first unit and the second unit are capable of communicating with each other. For example, rowing of a rowing boat having two seats can be simulated. Subsequent to starting of a specific training program, two users simultaneously using respective exercising devices have to synchronize their movements in order to row a virtual rowing boat. A first user is then virtually in the position of the person sitting in front of the other person. Thus, a sports team can train rowing of a rowing boat, for example in winter time when training with a real rowing boat is not possible due to weather conditions.

Figure 5:
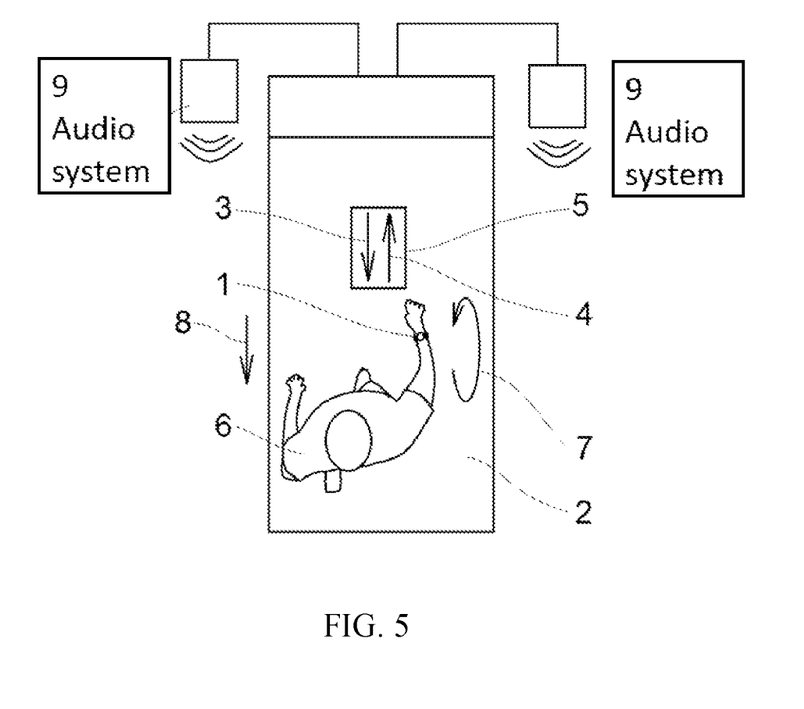
FIG. 5 illustrates a schematic top view of a mobile device comprised by a yet further arrangement in accordance with at least some embodiments of the present invention.

In FIG. 5 a schematic top view of a mobile device 1 comprised by a yet further arrangement in accordance with at least some embodiments of the present invention is illustrated. The exercising device 2 includes an audio system 9. Prior to pairing, indication that the mobile devices 1 and the exercising device 2 are engaged with each other has been provided to the exercising device 2 and the mobile device 1. After the pairing process 5 as described above in connection with FIG. 1, a music program can be started or stopped, a volume of music can be controlled and/or a title can be selected using the mobile device 1 in the form of a wrist-watch 1. According to this embodiment, the procedure is typically fully or at least partially controlled by the exercising device 2 such that no program code or a minimum amount thereof needs to be installed on the mobile device 1. The mobile device 1 serves as a user interface for the exercising device 2. In other words, a computer program comprising program instructions which, when loaded into the exercising device 2, cause e.g. graphical user interface data to be determined for the mobile device 1 is provided. The graphical user interface data is wirelessly transmitted to the mobile device 1 from the exercising device 2 to provide at least one user interface functionality on the mobile device 1. Then data corresponding to user input is received and wirelessly transmitted to the exercising device 2. Minimum system requirements such as processing capacity and memory capacity are required for the mobile device 1. According to this embodiment, the input data is completely or at least partially processed by the exercising device 2. The bidirectional communication link between the mobile device 1 and the exercising device 2 may be used to enable the exercising device 2 to act as a server having control over the user interface and the mobile device 1 to act as a client whose content is fully or at least partially controlled by the exercising device 2.

Alternatively, a provided further, second mobile device (not shown), for example a smartphone, may include an audio system. In such a case, a music program can be started or stopped, a volume of music can be controlled and/or a title can be selected using the wrist-watch 1 after the pairing process 5 between the mobile device 1 and the exercising device 2. In other words, the mobile device 1 may be used to additionally control functions of a further second mobile device. According to this embodiment, the procedure is typically fully or at least partially controlled by the second mobile device such that no program code or a minimum amount thereof needs to be installed on the mobile device 1 such as a wrist-watch. The mobile device 1 serves as a user interface for the second mobile device. In other words, a computer program comprising program instructions which, when loaded into the second mobile device, cause e.g. graphical user interface data to be determined for the mobile device 1 is provided. The graphical user interface data is wirelessly transmitted to the mobile device 1 from the second mobile device to provide at least one user interface functionality on the mobile device 1. Then data corresponding to user input is received and wirelessly transmitted to the second mobile device. Minimum system requirements such as processing capacity and memory capacity are required for the mobile device 1. According to this embodiment, the input data is completely or at least partially processed by the second mobile device. The bidirectional communication link between the mobile device 1 and the second mobile device may be used to enable the second mobile device to act as a server having control over the user interface and the mobile device 1 to act as a client whose content is fully or at least partially controlled by the second mobile device.

Figure 6:
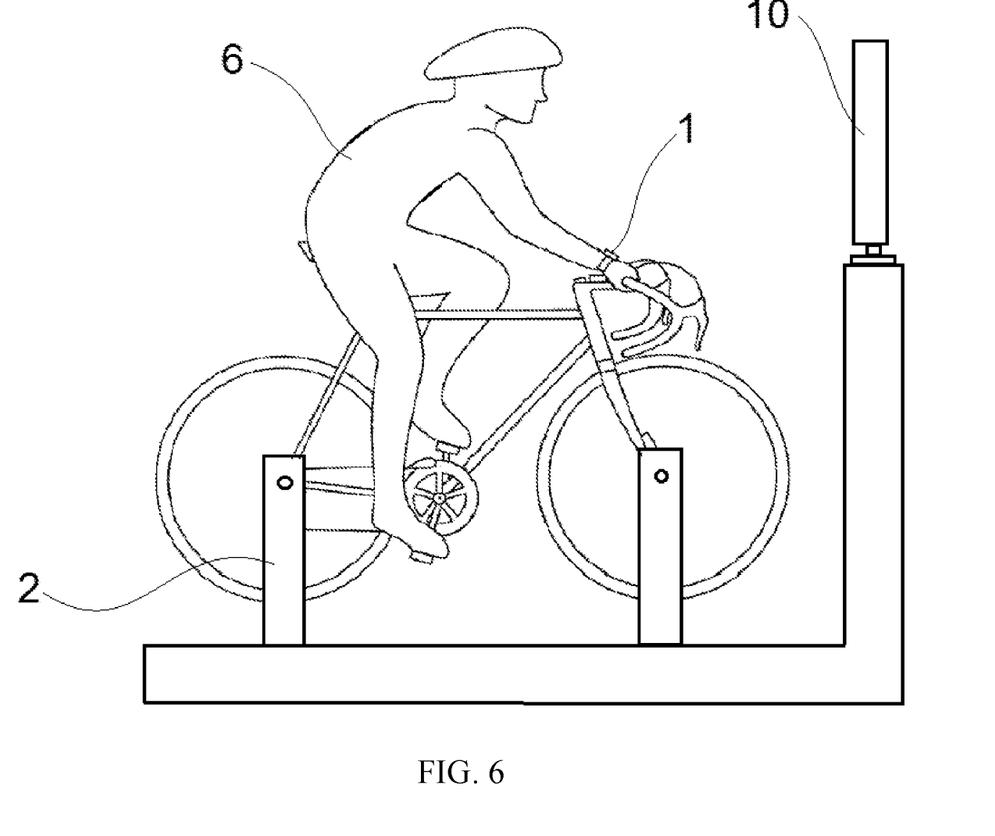
FIG. 6 illustrates a schematic side view of an exercising device comprised by a yet further arrangement in accordance with at least some embodiments of the present invention.

In FIG. 6 a schematic side view of an exercising device 2 comprised by a yet further arrangement in accordance with at least some embodiments of the present invention is illustrated. The shown exercising device 2 is an ergometer in the form of an indoor exercise bike. The exercising device 2 comprises at least one processing core and at least one memory including computer program code. The at least one memory and the computer program code are configured to, with the at least one processing core, cause the exercising device at least to transmit a first signal to an mobile device 1, receive a second signal from the mobile device 1, and participate in pairing with the mobile device 1. Prior to pairing, indication that the mobile devices 1 and the exercising device 2 are engaged with each other has been provided to the exercising device 2 and the mobile device 1. The exercising device 2 further comprises a video system 10. The video system 10 may be, for example, a TV, a tablet, or a PC. The mobile device 1 may be used as a remote control of the video system 10.

A wrist-watch is shown as the mobile device 1. Typically, the exercising device 2 is configured to transmit the first signal and to receive the second signal when a distance between the mobile device 1 and the exercise device 2 is about 0 m-10 m. In other words, the pairing process is activated when a user 6 with the wrist-watch 1 is moving closer to the exercising device 2. After the pairing process between the mobile device 1 and the exercising device 2, data can be transmitted between the mobile device 1 and the exercising device 2. For example, the user 6 may select a TV channel to be shown on the video system 10 by the wrist-watch 1. The wrist-watch 1 can therefore serve as a remote control when cycling. Alternatively, data obtained by sensors of the mobile device 1, for example heart beat data, and data obtained by sensors of the exercising device 2, for example speed data, may be displayed on the video system 10. The exercising device 2 is configured to participate in the pairing process during a session with the mobile device 1. The session is based on sensors of the mobile device 1 and the exercising device 2.

Figure 7:
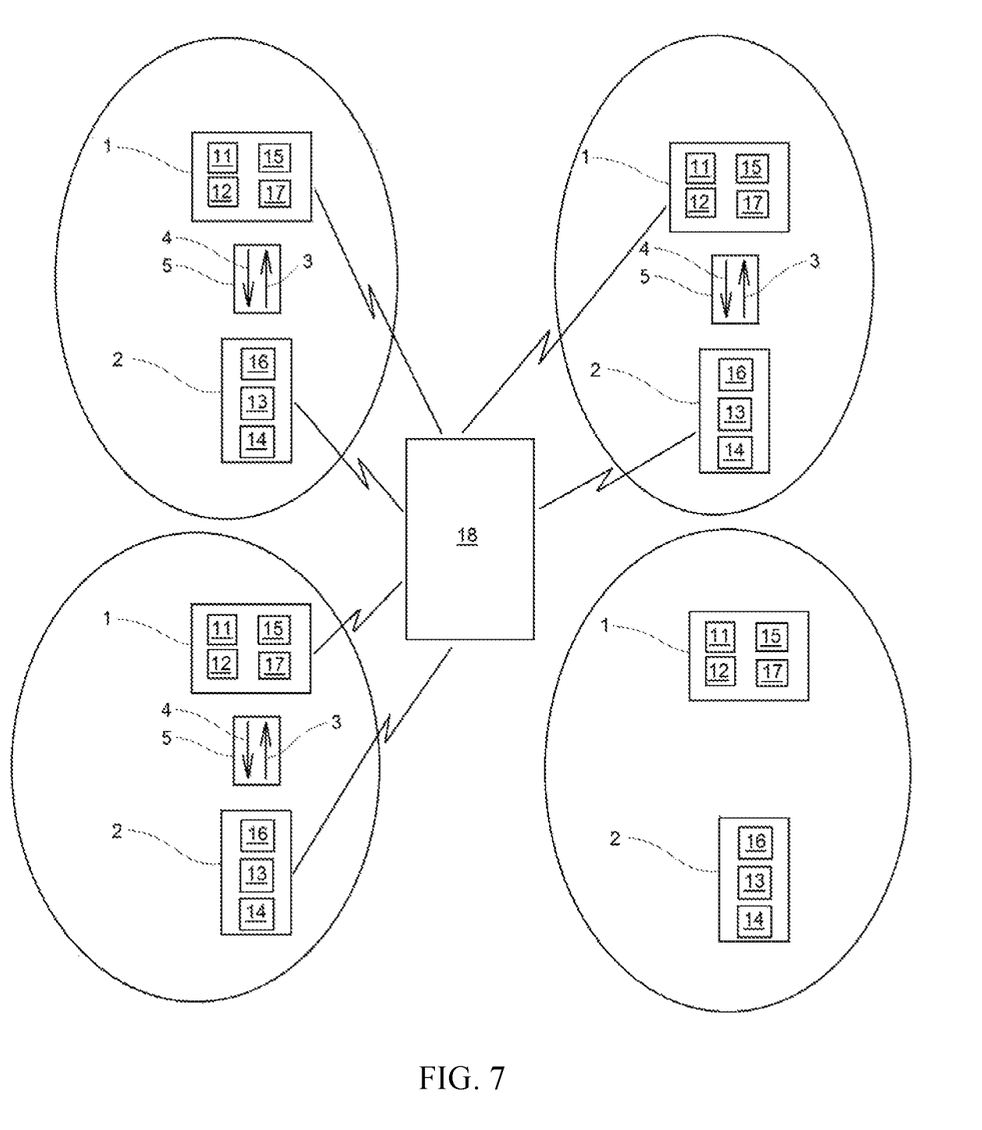
FIG. 7 illustrates a schematic view of an arrangement in accordance with at least some embodiments of the present invention.

In FIG. 7 a schematic view of an arrangement in accordance with at least some embodiments of the present invention is illustrated. FIG. 7 represents a situation in a gym with different exercising devices 2, for instance. The arrangement comprises an apparatus 18 comprising at least one processing core and at least one memory including computer program code. The at least one memory and the computer program code are configured to, with the at least one processing core, cause the apparatus 18 at least to receive a first sensor data stream from an exercising device 2, receive a second sensor data stream from a mobile device 1, correlate the first data stream with the second data stream, determine that the exercising device 2 is engaged with the mobile device 1, and provide indication to the exercising device 2 and the mobile device 1 that the devices 1, 2 are engaged with each other. In the shown example, four mobile devices 1 and four exercising devices 2 are illustrated. One mobile device 1 and one exercising device 2 form a single unit. In other words, four separate units are shown in FIG. 7. The apparatus 18 in the form of a server receives from three units a first sensor data stream from a sensor of the respective exercising device 2 and a second data stream from a sensor of a respective mobile device 1. For each unit, indication to the respective exercising device 2 and the respective mobile device 1 that the devices 1, 2 are engaged with each other is being provided and pairing between the devices 1, 2 of each unit can start. For each unit an activity type of a user, for example running, cycling and rowing, can be estimated. From the fourth unit no sensor data streams are received by the apparatus 18, i.e. the fourth unit is not in use and therefore no activity type can be estimated.

The server 18 is configured to estimate an activity type of different users based on the correlated data streams of a unit. In other words, the server 18 is capable of estimating if a person is cycling, running or rowing based on the correlated data. Data determined by sensors of each mobile device 1 and each respective exercising device 2 may be stored on the server. The server 18 is remotely accessible in order to analyse a user session at a later stage for each unit.

A user may use different exercising devices 2 in a gym, for example a treadmill first and then a cross trainer. Due to the correlated data streams and the time stamps associated with the sensor data contained in the data streams, thus e.g. indicating a start time and an end time of an activity type, pairing between a first exercising device and the mobile device can be automatically initiated first and pairing between a different second exercising device and the mobile device can be automatically initiated at a later stage.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in displaying of sensor data determined by at least one sensor of an exercising device and at least one sensor of a mobile device. Certain embodiments of the present invention are applicable in health care, in industry, in working environments, sports, etc.

REFERENCE SIGNS LIST 1 mobile device
2 exercising device
3 first signal
4 second signal
5 pairing
6 user
7 arrow
8 arrow
9 audio system
10 video system
11 processing core of mobile device
12 memory of mobile device
13 processing core of exercising device
14 memory of exercising device
15 display
16 sensor
17 user interface
18 apparatus

The invention claimed is:

1. A server comprising at least one processing core, at least one memory including computer program code, the at least one memory and the computer program code being configured to, with the at least one processing core, cause at least:
receiving by the server a first sensor data stream from a first exercising device, wherein the first sensor data stream comprises time stamps,
receiving by the server a second sensor data stream from a mobile device, wherein the second sensor data stream comprises time stamps,
correlating by the server the first sensor data stream with the second sensor data stream based on the time stamps comprised by the first sensor data stream and the time stamps comprised by the second sensor data stream,
determining by the server that the first exercising device is engaged with the mobile device, and
providing from the server indication to the first exercising device and the mobile device that the first exercising device and the mobile device are engaged with each other, and subsequently
receiving by the server a third sensor data stream from a second exercising device, wherein the third sensor data stream comprises time stamps,
receiving by the server a fourth sensor data stream from the mobile device, wherein the fourth sensor data stream comprises time stamps,
correlating by the server the third sensor data stream with the fourth sensor data stream based on the time stamps comprised by the third sensor data stream and the time stamps comprised by the fourth sensor data stream,
determining by the server that the second exercising device is engaged with the mobile device, and
providing from the server indication to the second exercising device and the mobile device that the second exercising device and the mobile device are engaged with each other, and
changing information displayed on a display of the mobile device automatically when the second exercising device is engaged with the mobile device,
wherein the correlating comprises identifying identical time stamps, and
wherein the server is configured to estimate that a user is using a specific exercising device by correlating sensor data received from the mobile device and sensor data received from said specific exercising device.

2. The server according to claim 1, wherein the server is configured to store and process sensor data received from the first exercising device and the second exercising device.

3. The server according to claim 1, wherein the server is configured to store and process sensor data received from the mobile device.

4. The server according to claim 1, wherein the first sensor data stream or the third sensor data stream is based on a first acceleration sensor and the second data stream or the fourth sensor data stream is based on a second acceleration sensor.

5. The server according to claim 1, wherein the first sensor data stream or the third sensor data stream is based on a first angular velocity sensor and the second data stream or the fourth sensor data stream is based on a second angular velocity sensor.

6. The server according to claim 1, wherein the server is configured to receive the first sensor data stream or the third sensor data stream from an ergometer, a gym exercising device, a fitness device, a sports device, a weight lifting device, an exercise bike, a treadmill, a rowing machine, or a cross trainer.

7. The server according to claim 1, wherein the server is configured to receive the second sensor data stream or the fourth sensor data stream from a tablet, a smartphone, a wearable sensor, or an external sensor.

8. The server according to claim 1, wherein the server is configured to receive a fifth sensor data stream from a wearable sensor or an external sensor.

9. The server according to claim 1, wherein the server is configured to allow a user to remotely read-out at least a part of at least one of the first sensor data stream, the second sensor data stream, the third sensor data stream and the fourth sensor data stream.

10. The server according to claim 1, wherein the server is remotely accessible by a person in order to analyse a user session.

11. The server according to claim 1, wherein the server is configured to estimate an activity type of a user based on the correlated data streams.

12. The server according to claim 1, wherein the server is configured to receive the second sensor data stream or the fourth sensor data stream from a wrist-watch.

13. The server according to claim 1, wherein the server is configured to receive the second sensor data stream or the fourth sensor data stream from a smartwatch.

14. The server according to claim 1, wherein the first exercising device, the second exercising device and the mobile device each have a classification task to produce semantic events.

15. The server according to claim 1, wherein the server is in the form of a mobile device.

16. The server according to claim 8, wherein any of the first exercising device, and the second exercising device are enabled to act as a server having control over the user interface of the mobile device.

17. Use of a server in connection with a first exercising device, a second exercising device and a mobile device, wherein the server comprises at least one processing core, at least one memory including computer program code, the at least one memory and the computer program code being configured to, with the at least one processing core, cause at least:
receiving by the server a first sensor data stream from a first exercising device, wherein the first sensor data stream comprises time stamps,
receiving by the server a second sensor data stream from a mobile device, wherein the second sensor data stream comprises time stamps,
correlating by the server the first sensor data stream with the second sensor data stream based on the time stamps comprised by the first sensor data stream and the time stamps comprised by the second sensor data stream,
determining by the server that the first exercising device is engaged with the mobile device, and
providing from the server indication to the first exercising device and the mobile device that the first exercising device and the mobile device are engaged with each other, and subsequently
receiving by the server a third sensor data stream from a different second exercising device, wherein the third sensor data stream comprises time stamps,
receiving by the server a fourth sensor data stream from the mobile device, wherein the fourth sensor data stream comprises time stamps,
correlating by the server the third sensor data stream with the fourth sensor data stream based on the time stamps comprised by the third sensor data stream and the time stamps comprised by the fourth sensor data stream,
determining by the server that the second exercising device is engaged with the mobile device, and
providing from the server indication to the second exercising device and the mobile device that the second exercising device and the mobile device are engaged with each other, and
changing information displayed on a display of the mobile device automatically when the second exercising device is engaged with the mobile device,
wherein the correlating comprises identifying identical time stamps, and
wherein the server is configured to estimate that a user is using a specific exercising device by correlating sensor data received from the mobile device and sensor data received from said specific exercising device.

18. The use according to claim 17, wherein the use takes place in a gym, in connection with a training session, in connection with a sports session or in connection with a fitness session.

19. An arrangement comprising a server, a first exercising device, a second exercising device and a mobile device, wherein the server comprises at least one processing core, at least one memory including computer program code, the at least one memory and the computer program code being configured to, with the at least one processing core, cause at least:
receiving by the server a first sensor data stream from a first exercising device, wherein the first sensor data stream comprises time stamps,
receiving by the server a second sensor data stream from a mobile device, wherein the second sensor data stream comprises time stamps,
correlating by the server the first sensor data stream with the second sensor data stream based on the time stamps comprised by the first sensor data stream and the time stamps comprised by the second sensor data stream,
determining by the server that the exercising device is engaged with the mobile device, and
providing from the server indication to the first exercising device and the mobile device that the first exercising device and the mobile device are engaged with each other, and subsequently
receiving by the server a third sensor data stream from a different second exercising device, wherein the third sensor data stream comprises time stamps,
receiving by the server a fourth sensor data stream from the mobile device, wherein the fourth sensor data stream comprises time stamps,
correlating by the server the third sensor data stream with the fourth sensor data stream based on the time stamps comprised by the third sensor data stream and the time stamps comprised by the fourth sensor data stream,
determining by the server that the second exercising device is engaged with the mobile device, and
providing from the server indication to the second exercising device and the mobile device that the second exercising device and the mobile device are engaged with each other, and
changing information displayed on a display of the mobile device automatically when the second exercising device is engaged with the mobile device,
wherein the correlating comprises identifying identical time stamps, and
wherein the server is configured to estimate that a user is using a specific exercising device by correlating sensor data received from the mobile device and sensor data received from said specific exercising device.

20. The arrangement according to claim 19, wherein the exercising device and the second exercising device are configured to participate in pairing with the mobile device.

21. The arrangement according to claim 19, wherein the mobile device is configured to participate in pairing with the first exercising device and the second exercising device during a session with the first and second exercising devices.

* * * * *